United States Patent
Tzodikov (12)

(10) Patent No.: US 6,346,547 B1
(45) Date of Patent: Feb. 12, 2002

(54) N-SUBSTITUTED AMINO ACIDS, ANTIOXIDANT PHARMACEUTICAL COMPOSITIONS CONTAINING N-SUBSTITUTED AMINO ACIDS AND METHODS FOR PREVENTING CARDIOVASCULAR DISEASES AND/OR PREVENTING AND/OR TREATING ANTIOXIDANT RESPONSIVE DISEASES THEREWITH

(75) Inventor: Nathan Tzodikov, Haverford, PA (US)

(73) Assignee: Checkpoint, Genetics, Inc., Exton, PA (US)

( * ) Notice: Subject to any disclaimer, the term of this patent is extended or adjusted under 35 U.S.C. 154(b) by 0 days.

(21) Appl. No.: 09/500,064

(22) Filed: Feb. 8, 2000

Related U.S. Application Data

(60) Provisional application No. 60/119,030, filed on Feb. 8, 1999, and provisional application No. 60/167,069, filed on Nov. 23, 1999.

(51) Int. Cl.[7] .................. A61K 31/98; A61K 31/40; A61K 31/445; A61P 25/28; C07C 229/22
(52) U.S. Cl. .................. 514/551; 514/212; 514/315; 514/423; 514/561; 514/614; 514/626; 514/665; 548/532; 548/537; 558/252; 560/170; 564/151; 564/198; 562/567
(58) Field of Search .................. 514/212, 315, 514/423, 551, 561, 614, 626, 665, 217.11; 548/532, 537, 530; 558/252; 560/170; 562/567; 564/151.198

(56) References Cited

U.S. PATENT DOCUMENTS

| | | | |
|---|---|---|---|
| 2,017,537 A | 10/1935 | Hoffman et al. ............. 560/170 |
| 2,368,208 A | 1/1945 | Epstein et al. ............... 554/106 |
| 3,567,752 A | * 3/1971 | Israily ......................... 556/148 |
| 3,872,116 A | 3/1975 | Gipson ........................ 544/170 |
| 4,358,434 A | 11/1982 | Tzodikov et al. ............. 521/25 |
| 4,385,068 A | 5/1983 | Kendall et al. ............... 514/561 |
| 4,390,517 A | 6/1983 | O'Brien et al. .............. 424/1.45 |
| 4,418,060 A | 11/1983 | László et al. ................ 514/152 |
| 4,518,608 A | 5/1985 | Kahan ......................... 514/420 |
| 4,639,468 A | * 1/1987 | Roncucci et al. ............ 514/620 |
| 4,868,161 A | 9/1989 | Roberts ........................ 514/49 |
| 4,925,860 A | 5/1990 | Herbranson et al. ......... 514/359 |
| 5,026,728 A | 6/1991 | Kendal et al. ................ 514/561 |
| 5,080,886 A | 1/1992 | Mickle et al. ................ 514/311 |
| 5,326,757 A | 7/1994 | Demopoulos ................ 514/167 |
| 5,350,837 A | * 9/1994 | Bridger et al. ............... 534/14 |
| 5,480,645 A | 1/1996 | Della Valle et al. ......... 424/439 |
| 5,480,909 A | 1/1996 | Stanko ......................... 514/557 |
| 5,506,266 A | 4/1996 | Davies et al. ................ 514/575 |
| 5,679,711 A | 10/1997 | Carrell et al. ................ 514/557 |
| 5,721,131 A | * 2/1998 | Rudolph et al. ....... 435/240.243 |
| 5,731,349 A | 3/1998 | Komissarova et al. ....... 514/561 |
| 5,741,893 A | 4/1998 | Hsia ............................ 530/385 |
| 5,744,120 A | 4/1998 | Edwards et al. ............. 424/1.64 |
| 5,750,351 A | 5/1998 | Medford et al. ............ 435/7.21 |
| 5,756,492 A | 5/1998 | Buelow et al. ............... 514/185 |
| 5,773,209 A | 6/1998 | Medford et al. ............ 435/7.24 |
| 5,773,231 A | 6/1998 | Medford et al. ............ 435/7.24 |
| 5,783,596 A | 7/1998 | Medford et al. ............. 514/423 |
| 5,792,444 A | 8/1998 | Fischman et al. ........... 424/1.69 |
| 5,792,787 A | 8/1998 | Medford et al. ............. 514/423 |
| 5,807,884 A | 9/1998 | Medford et al. ............. 514/423 |
| 5,811,449 A | 9/1998 | Medford et al. ............. 514/423 |
| 5,821,260 A | 10/1998 | Medford et al. ............. 514/423 |
| 5,824,781 A | 10/1998 | Hsia ............................ 530/385 |
| 5,846,959 A | 12/1998 | Medford et al. ............. 514/165 |
| 5,854,287 A | 12/1998 | Weglicki ..................... 514/569 |
| 5,872,101 A | 2/1999 | Munoz et al. ................ 514/18 |
| 5,874,468 A | 2/1999 | Atlas et al. .................. 514/597 |
| 5,879,659 A | 3/1999 | Edwards et al. ............ 429/1.69 |
| 5,965,695 A | 10/1999 | Simon et al. ................ 530/324 |
| 5,989,557 A | * 11/1999 | Bombardelli et al. .... 427/195.1 |

FOREIGN PATENT DOCUMENTS

| | | |
|---|---|---|
| GB | 2059768 | 4/1981 |
| WO | WO 97/41847 | 11/1997 |
| WO | WO 98/29375 | 7/1998 |

OTHER PUBLICATIONS

Chemical Abstract 73:127,782u, Hypotensive Contituents of marine algae, 1970.*

Paul Simpson, et al., "Free Radicals and Myocardial Ischemia and Reperfusion Injury", *J. Lab Clin Med*, vol. 110 No. 1, pp. 13–30 (1987).

(List continued on next page.)

*Primary Examiner*—Jeffrey E. Russell
(74) *Attorney, Agent, or Firm*—Venable; Michael A. Gollin; Keith G. Haddaway

(57) ABSTRACT

Low-toxicity, highly-bioavailable, pharmaceutical antioxidant compositions for preferred oral administration to mammals are provided which have at least one amino acid-based compound of the general formula (I):

$$A-N(Z)-CH(R^1)C(O)-Q \qquad (I)$$

wherein A is represented by the formula:

$$XO-[C(R^2)_2]_n-$$

wherein n is an integer of from 1 to about 3, X is selected from the group consisting of a hydrogen atom, an acyl group and a halogenated acyl group and each $R^2$ is independently selected from the group consisting of a hydrogen atom, an alkyl group having from 1 to about 3 carbon atoms, a hydroxyalkyl group having from 1 to about 3 carbon atoms, and $CH_2OX$; Z is selected from the group consisting of a hydrogen atom, an alkyl group of from 1 to about 3 carbon atoms, and A; $R^1$ is an amino acid side chain group or an amino acid side chain group which forms with $R^2$ a single heterocyclic structure having a total of from 5 to 7 atoms in the ring; and wherein Q is a substituent selected from the group consisting of a hydroxyl, $-N(R^2)_2$, $-NR^2(NR^2)_2$, $-SR^2$, an alkoxy, a halogenated alkoxy, an O-acyl and an O-halogenated acyl are disclosed. Methods of treating, delaying the onset of and/or preventing antioxidant responsive diseases comprising administering such pharmaceutical antioxidant compositions and amino acid-based compounds of the general formula (I) are also disclosed.

34 Claims, No Drawings

OTHER PUBLICATIONS

Jay H. Kramer, et al., "Lipid Peroxidation–Derived Free Radical Production and Postischemic Myocardial Reperfusion Injury", *Anals New York Academy of Sciences*, pp. 180–196 (no date indicated).

Dennis L. Sprecher, et al., "Cardiovascular Features of Homozygous Familial Hypercholesterolemia: Analysis of 16 Patients", *The American journal of Cardiology*, vol. 54, pp. 20–30 (1984).

Thomas E. Carew, et al., "Antiatherogenic Effect of Probucol Unrelated to its Hypocholesterolemic Effect: Evidence That Antioxidants in vivo Can Selectively Inhibit Low Density Lipoprotein Degradation in Macrophage–Rich Fatty Streaks and Slow The Progresion of Atherosclerosis in the Watanabe Heritable Hyperlipidemic Rabbit", *Proc. Natl. Acad. Sci. USA*, vol. 84, pp. 7725–7728 (1987).

Claudio Napoli, et al., "Oxidative Structural Modifications of Low Density Lipoprotein in Homozygous Familial Hypercholesterolemia", *Atherosclerosis*, vol. 118, pp. 259–273 (1995).

A. Jackie Hunter, et al., "Animal Models of Acute Ischaemic Stroke: Can They Predict Clinically Successful Neuroprotective Drugs?" *TiPS*, vol. 16, pp. 123–128 (1995).

Judith A. Berliner, et al., "The Role of Oxidized Lipoproteins in Atherogenesis" *Free Radical Biology & Medicine*, vol. 20, pp. 707–727 (1996).

Aklaq A. Farooqui, et al., "Lipid Peroxides in the Free Radical Pathophysiology of Brain Diseases" *Cellular and Molecular Neurobiology*, vol. 18, No. 6, pp. 599–608 (1998).

Yvonne Y.C. Lo, et al., "Reactive Oxygen Species Mediate Cytokine Activation of c–Jun $NH_2$–terminal Kinases" *The Journal of Biological Chemistry*, vol. 271, No. 26, pp. 15703–15707 (1996).

Sigma–Aldrich, Inc., "Sigma Product Information Sheet for Tricine" (1996) (2 pages).

Ira Shoulson, "Experimental Therapeutics of Neurodegenerative Disorders: Unmet Needs", *Sciences*, vol. 282, pp. 1072–1074 (1998).

Suresh S. Pitchumoni, "Current Status of Antioxidant Therapy for Alzheimer's Disease", *JAGS—The American Geriatrics Society*, vol. 46, pp. 1566–1572 (1998).

Rebecca Rawls, "When Neurons Go Awry—Oxidants Stress, Role of NO Among Possible Causes of Neurodegenrative Diseases Being Investigated," *C&EN*, pp. 78–80 (1998).

Jaffer Nourooz–Zadeh, "Ferrous Ion Oxidation in Presence of Xylenol Orange for Detection of Lipid Hydroperoxides in Plasma," *Methods in Enzymology*, vol. 300, pp. 58–62 (1999).

Zhen–Yue Jiang, et al., "Ferrous Ion Oxidation in the Presence of Xylenol Orange for Detection of Lipid Hydroperoxide in Low Density Lipoprotein", *Analytical Biochemistry*, vol. 202, pp. 384–389 (1992).

Norman E. Good, et al., "Hydrogen Ion Buffers for Biological Research", *Biochemistry*, vol. 5, No. 2 (1966) pp. 467–477.

P.J. Simpson, et al., "Free Radicals and Myocardial Ischemia and Reperfusion Injury", *Lab Clin Med*, (Abstract only www.ncbi.com)(1987).

Maarten C. de Rijk, et al. "Dietary Antioxidants and Parkinson Disease", *Arch Neurol*, vol. 54, pp. 762–765 (1997).

Yu Yamaguchi, et al., "Enhancement of Aortic Cholesterol Deposition by Dietary Linoleic Acid in Cholestrol–Fed Mice: an Animal Model For Primary Screening of Antiatherosclerotic Agents" *Journal of Pharmacological and Toxicological Methods*, vol. 30, pp. 169–175 (1993).

L.R. Williams, "Oxidative Stress, Age Related Neurodegeneration, and the Potential For Neurotrophic Treatment" Cerebrovasc, Brian Metab, (Rev., Abstract only www.ncbi.com)(1995).

Russell Ross, the Pathogenesis of Atherosclerosis: A Perspective for the 1900's, *Nature*, vol. 362, pp. 801–809 (1993).

XP–002138737: J. Bolós et al. "Studies on the Hydrogenation of 6–(Hydroxymethyl)pyridine–2–carboxylates and its Application to the Synthesis of 6–(Hydroxymethyl)piperidine–2–carboxylic Acid Derivatives"; *Journal fo Heterocyclic Chemistry*; vol. 31, No. 6, 1994; pp. 1493–1496.

XP–002138738: D.S. Kemp, et al. "Stereoselective Decarboxylation of a Geminal Dicarboxylic Acid. Synthesis of cis–5–(Hydroxymethyl)–D–proline Derivatives"; *Journal of Organic Chemistry*; vol. 51, No. 12, 1986; pp. 2377–2378.

XP–004056636: J.W. Suggs et al. "Facile Hydrolysis and Formation of Amide Bonds by N–Hydroxyethylation of α–Amino Acids"; *Tetrahedron Letters*; vol. 38, No. 13, 1997; pp. 2227–2230.

Xp–000611235: R. Tomatis et al. "Synthesis and Pharmacological Activity of Leu–Enkephalins Modified at $Gly^2$–$Gly^3$ Nitrogens"; *European Journal of Medical Chemistry*; vol. 16, No. 3, 1981; pp. 229–232.

XP–002138739: S–E. Yoo, et al. "An Efficient Synthesis of the Basic Pyrrolidine Ring for the Kainoids"; *Tetrahedron Letters*; vol. 29, No. 18, 1988; pp. 2195–2196.

* cited by examiner

N-SUBSTITUTED AMINO ACIDS, ANTIOXIDANT PHARMACEUTICAL COMPOSITIONS CONTAINING N-SUBSTITUTED AMINO ACIDS AND METHODS FOR PREVENTING CARDIOVASCULAR DISEASES AND/OR PREVENTING AND/OR TREATING ANTIOXIDANT RESPONSIVE DISEASES THEREWITH

CROSS-REFERENCE TO RELATED APPLICATIONS

This patent application claims the benefit of U.S. Provisional Patent Application No. 60/119,030, filed on Feb. 8, 1999, and No. 60/167,069, filed on Nov. 23, 1999.

BACKGROUND OF THE INVENTION

A common phenomenon associated with disease etiology is the overproduction of an undesired metabolic byproduct. Although mammalian life requires molecular oxygen ($O_2$), the normal metabolic pathway for oxygen clearance involves a one-electron reduction to superoxide ($O_2^-$). Even though natural processes exist to render this superoxide harmless, they are often out of balance, leading to several serious diseases initiated by chronic buildup of the effects of reactive oxygen.

Natural antioxidants are available through consumption of a nutritious diet, by consumption of specific nutritional supplements and prescription pharmaceutical preparations. A factor governing the effectiveness of this lifestyle and therapy is their abundance and absorption after oral ingestion, limiting their local concentration in circulation. Overall, the number and variety of antioxidant compositions is rather large.

However, while some antioxidant compositions are capable of reducing physiological oxidation within the human body, most compounds do not possess the requisite low-toxicity, high-bioavailability, and/or versatility that a desirable dietary supplement should possess. Generally, anti-oxidant compositions function as substrates which are more easily oxidized than the substances which would otherwise be attacked (i.e., the body's cells). In effect, an antioxidant composition provides for the preferential oxidation of itself as opposed to cells. Unfortunately, some antioxidant compositions used to treat certain diseases and ailments are unable to provide the desired low degree of toxicity, high bioavailability and/or the versatility to treat a wide variety of diseases.

Some substances, which are generally referred to as free-radical scavengers, have the ability to reduce oxidation by being more easily oxidized themselves, however, many are too toxic for ingestion. Other compounds which are both anti-oxidants and non-toxic suffer from an inability to reach certain portions of the body due to their solubility properties. For example, vitamin E is generally lipid-soluble yet not very water-soluble. Analogs of vitamin E which are water-soluble have been prepared. However, in some instances, these analogs are either toxic or less effective than the vitamin itself.

The preparation of therapeutic antioxidant agents and the development of treatments using antioxidant therapeutic agents continues to be an area of interest in preventing and/or treating various antioxidant responsive diseases. Such diseases include a wide variety of antioxidant responsive diseases such as the use of antioxidants in the treatment of central nervous system neurodegenerative disorders such as Parkinson's, Alzheimer's and Creutzfeldt-Jakob's diseases.

Antioxidants have been used for treating other conditions of peripheral tissues, such as acute respiratory distress syndrome, amyotrophic lateral sclerosis, atherosclerotic cardiovascular disease and multiple organ disfunction. Correlative pathways between oxidative stress and various neurodegenerative pathologies have also been found. For example, evidence has been accumulated which connects oxidative stress with pathogenesis of Parkinson', Alzheimer's, Creutzfeldt-Jakob's diseases and other human neurodegenerative disorders. See U.S. Pat. No. 5,874,468. These studies were initiated since auto-oxidation of levodopa and dopamine are known to produce oxygen free radicals and, peroxides, quinones and semiquninones.

In addition to these diseases, antioxidants have been used for treatment of oxidant injury, particularly in reperfusion injury which has been observed to occur upon reperfusion following ischemia caused, for example, by blood clots, organic repair and transplant surgery. A number of causes and mechanisms have been suggested for the damage that occurs to tissue after ischemia and reperfusion. While it is likely that a variety of causes and mechanisms contribute to the damage, a popular current theory that is supported by experimental evidence involves the generation of free radicals upon reperfusion. See U.S. Pat. No. 5,080,886, incorporated herein by reference, wherein the current consensus on the role of free radicals in reperfusion injury in the heart is discussed in the various articles cited therein.

While the positive effects of antioxidants for treatment of the above noted and other antioxidant responsive diseases is known, there continues to be a need in the art for therapeutic antioxidant agents for use in pharmaceutical antioxidant compositions which possess low toxicity, high bioavailability and which are able to treat a wide variety of diseases and/or ailments.

BRIEF SUMMARY OF THE INVENTION

The present invention includes amino acid-based compounds of the general formula (I):

$$A\text{—}N(Z)\text{—}CH(R^1)C(O)\text{—}Q \qquad (I)$$

wherein A is represented by the formula:

$$XO\text{—}[C(R^2)_2]_n\text{—}$$

wherein n is an integer of from 1 to about 3, X is selected from the group consisting of a hydrogen atom, an acyl group and a halogenated acyl group and each $R^2$ is independently selected from the group consisting of a hydrogen atom, an alkyl group having from 1 to about 3 carbon atoms and a hydroxyalkyl group having from 1 to about 3 carbon atoms, and $CH_2OX$; Z is selected from the group consisting of a hydrogen atom, an alkyl group of from 1 to about 3 carbon atoms, and A; $R^1$ is selected from an amino acid side chain group or an amino acid side chain group which forms with $R^2$ a single heterocyclic ring structure having a total of from 5 to 7 atoms in the ring; and Q is a substituent selected from the group consisting of —$N(R^2)_2$, —$NR^2N(R^2)_2$, —$SR^2$, an alkoxy, a halogenated alkoxy, an O-acyl and an O-halogenated acyl.

The present invention also includes amino acid-based compounds of the general formula (I)

$$A\text{—}N(Z)\text{—}CH(R^1)C(O)\text{—}Q \qquad (I)$$

wherein A is represented by the formula:

$$XO\text{—}[C(R^2)_2]_n\text{—}$$

wherein n is an integer of from 1 to about 3, X is selected from the group consisting of a hydrogen atom, an acyl group and a halogenated acyl group and each $R^2$ is independently selected from the group consisting of a hydrogen atom, an alkyl group having from 1 to about 3 carbon atoms and a hydroxyalkyl group having from 1 to about 3 carbon atoms, and $CH_2OX$; Z is selected from the group consisting of a hydrogen atom, an alkyl group of from 1 to about 3 atoms, and A; $R^1$ is an amino acid side chain group which forms with $R^2$ a single heterocyclic ring structure having a total of from 5 to 7 atoms in the ring; and Q is a substituent selected from the group consisting of a hydroxyl, —$N(R^2)_2$, $NR^2N(R^2)_2$, —$SR^2$, an alkoxy, a halogenated alkoxy, an O-acyl and an O-halogenated acyl.

In one embodiment, the invention includes amino-acid based compounds in accordance with formula (I) above in which Z is a hydrogen atom, $R^1$ is a hydrogen atom and A is —$C(CH_2OH)_3$, wherein Q is is a substituent selected from the group consisting of —$N(R^2)_2$, —$NR^2N(R^2)_2$, —$SR^2$, an alkoxy, a halogenated alkoxy, an O-acyl and an O-halogenated acyl.

Additionally, the present invention includes low-toxicity, highly-bioavailable, pharmaceutical antioxidant compositions for administration to mammals, said pharmaceutical antioxidant compositions comprising an amino acid-based compound of the general formula (I)

A—N(Z)—CH($R^1$)C(O)—Q       (I)

wherein A is represented by the formula:

wherein n is an integer of from 1 to about 3, X is selected from the group consisting of a hydrogen atom, an acyl group and a halogenated acyl group and each $R^2$ is independently selected from the group consisting of a hydrogen atom, an alkyl group having from 1 to about 3 carbon atoms and a hydroxyalkyl group having from 1 to about 3 carbon atoms, and $CH_2OX$; Z is selected from the group consisting of a hydrogen atom, an alkyl group of from 1 to about 3 carbon atoms and A; $R^1$ is selected from an amino acid side chain group and an amino acid side chain group in which forms with $R^2$ a single heterocyclic ring structure having a total of from 5 to 7 atoms in the ring; and wherein Q is a substituent selected from the group consisting of a hydroxyl, —$N(R^2)_2$, —$NR_2(R_2)_2$, —$SR^2$, an alkoxy, a halogenated alkoxy, an O-acyl and an O-halogenated acyl.

Furthermore, the present invention includes a method of treating, delaying the onset of and/or preventing antioxidant-responsive diseases in mammals, said method comprising administering a pharmaceutical antioxidant composition comprising a therapeutically effective amount of an amino acid-based compound of the general formula (I)

A—N(Z)—CH($R^1$)C(O)—Q       (I)

wherein A is represented by the formula:

wherein n is an integer of from 1 to about 3, X is selected from the group consisting of a hydrogen atom, an acyl group and a halogenated acyl group and each $R^2$ is independently selected from the group consisting of a hydrogen atom, an alkyl group having from 1 to about 3 carbon atoms and a hydroxyalkyl group having from 1 to about 3 carbon atoms, and $CH_2OX$; Z is selected from the group consisting of a hydrogen atom, an alkyl group of from 1 to about 3 carbon atoms, and A; $R^1$ is selected from an amino acid side chain group and an amino acid side chain group in which forms with $R^2$ a single heterocyclic ring structure having a total of from 5 to 7 atoms in the ring; and wherein Q is a substituent selected from the group consisting of a hydroxyl, —$N(R^2)_2$, —$NR_2(R_2)_2$, —$SR^2$, an alkoxy, a halogenated alkoxy, an O-acyl and an O-halogenated acyl.

In preferred embodiments of the invention as described above and in detail hereinafter, preferred antioxidant pharmaceutical compositions include an amino acid-based compound selected from bicine, tricine and/or carboxylic acid derivatives thereof, such as ethyl esters of tricine and bicine. The method according to the present invention preferably comprises administering an antioxidant composition comprising a therapeutically effective amount of an amino acid-based compound selected from bicine, tricine and/or carboxylic acid derivatives thereof, such as ethyl esters of tricine and bicine. Furthermore, the method according to the present invention is preferably accomplished via oral administration.

DETAILED DESCRIPTION OF THE INVENTION

The present invention includes N-substituted amino acid-based compounds, pharmaceutical antioxidant compositions comprising N-substituted amino acid-based compounds and methods of treating antioxidant responsive diseases via administration of an pharmaceutical antioxidant composition comprising at least one N-substituted amino acid-based compound as described herein.

As used herein, the phrase "amino acid-based compound" refers to any chemical compound having at least a portion of its structure corresponding to any of the various amino acids, including but not limited to any of the known twenty-two common amino acids, including aspartic acid, glutamic acid, lysine, arginine, histidine, tyrosine, cysteine, asparagine, glutamine, serine, threonine, glycine, alanine, valine, leucine, isoleucine, methionine, proline, phenylalanine, tryptophan, cystine, and hydroxyproline, with the exception that the amino functionality and/or the carboxylic acid functionality thereof are preferably derivatized, as discussed below in greater detail. Use of the phrase "amino acid-based compound" does not require that the compound be derived from or prepared from an amino acid.

Amino acid-based compounds for use in pharmaceutical antioxidant compositions in accordance with the present invention have the general formula (I), as set forth above. In general formula (I), the substituent A is represented by XO—$[C(R^2)_2]_n$ and the substituent Z is hydrogen or may also be represented by A or by a lower alkyl group of from one to about 3 carbon atoms. It will be understood, in accordance with this disclosure, that lower alkyl groups such as those referred to herein having from 1 to about 3 carbon atoms are preferred, however, it is within the scope of the invention that alkyl groups of from 1 to about 3 carbon atoms may also include substitutions of the hydrogens on the chain with other lower alkyl groups as well as encompassing within the scope of from 1 to about 3 carbon atoms other lower alkyl groups of up to 5 or even 7 carbon atoms. In all instances, X may be a hydrogen atom, an acyl group or a halogenated acyl group. Acyl groups which may be present include those of the general formula R'C(O)—, wherein R' represents a hydrocarbon group, for example a straight or branched chain alkyl, a cycloalkyl, a straight or branched chain alkenyl, or an aromatic hydrocarbon, in which R' preferably has from 1 to about 15 carbon atoms, However, R' more preferably includes hydrocarbon groups having about 5 or fewer carbon atoms for optimizing the absorption of the amino acid-based compound. The halogenated acyl groups which may be present include those acyl groups described above wherein one or more hydrogen atoms in the R' group have been substituted with a halogen atom, for example chlorine, bromine, iodine, fluorine and astatine.

The integer n is preferably 1, 2, or 3. More preferably, n represents the integer 2 or 3, and most preferably n equals 2. As discussed in more detail below, it is most preferred for n to equal 2 because of the exceptional ability of such compounds to form a stable nitroxyl radical, due to the interatomic distance of the hydroxyl group in A from the nitroxyl oxygen.

In general formula (I), each $R^2$ independently represents a hydrogen atom, an alkyl group preferably having from 1 to about 3 carbon atoms or a hydroxyalkyl group preferably having from 1 to about 3 carbon atoms and $CH_2OX$, in which X is as defined elsewhere herein. Alkyl groups which may be present include, for example, methyl, ethyl, propyl and isopropyl. Hydroxyalkyl groups include similar alkyl groups bearing at least one hydroxy group on one or more of the carbon atoms.

$R^1$ is preferably either an amino acid side chain group or, in certain preferred embodiments of the invention, $R^1$ is an amino acid side chain group which with $R^2$ forms a heterocyclic ring structure as described further below. The phrase "amino acid side chain group" as used herein, refers the common amnio acid functional "R" side chains of any amino acid, including the twenty two amino acids noted above, i.e., the substituents on the amino acid carbon atom located between the amino group and carboxylic acid functionalities of the amino acids, as described above. For example, typical side chains which would result in the above-noted amino acids include thioalkyl, indole, phenyl, hydroxy phenyl, carboxylic acid, guanidinum terminated alkyl, and imidizole terminated alkyl.

In general formula (I), as noted above, $R^1$ and an $R^2$ substituent may also form a heterocyclic ring structure having a total of from about 5 to about 7 atoms in the ring. For example, the nitrogen atom of general formula (I), along with —C—$R^2$— from the substituent represented by A and —C—$R^1$—, may form a pyrrolidine or a hydroxypyrrolidine ring, in which case the total number of carbon atoms in $R^1$ and the $R^2$ group equals 2 and the total number of atoms in the ring is 5, or a piperidine ring, in which case the total number of carbon atoms in $R^1$ and the $R^2$ group equals 3 and the total number of atoms in the ring is 6.

In general formula (I), Q represents a wide variety of substituents. For example, Q can represent a hydroxyl moiety such that the amino acid based compound possesses a carboxylic acid functionality. In certain preferred embodiments of the amino acid-based compounds of the invention, Q is not hydroxy when $R^1$ and $R^2$ are not in a ring structure. Additionally, Q may represent —$N(R^2)_2$, —$NRN(R^2)_2$, —$SR^2$, an alkoxy, a halogenated alkoxy, an O-acyl or an O-halogenated acyl, wherein $R^2$ is the same as described above. Alkoxy substituents which may be present include those of the general formula —OR", wherein R" represents a hydrocarbon group, for example a straight or branched chain alkyl, a cycloalkyl, a straight or branched chain alkenyl, or an aromatic hydrocarbon, in which R" preferably has from 1 to about 14 carbon atoms. However, R" more preferably has about 6 or fewer carbon atoms for the purposes optimizing the absorption of the amino acid-based compound. The halogenated alkoxy groups which may be present include those alkoxy groups described above wherein one or more hydrogen atoms in the R" group have been substituted with a halogen atom.

Q may also represent an O-acyl or an O-halogenated acyl group of the general formula —OC(O)R''', wherein R''' represents a hydrocarbon group, for example a straight or branched chain alkyl, a cycloalkyl, a straight or branched chain alkenyl, or an aromatic hydrocarbon, wherein R''' preferably has from 1 to about 14 carbon atoms. However, R''' more preferably has about 6 or fewer carbon atoms for the purposes of optimizing the absorption of the amino acid-based compound. The O-halogenated acyl groups which may be present include those O-acyl groups described above wherein one or more hydrogen atoms in the R''' group have been substituted with a halogen atom. Preferably, where a hydrogen has been substituted with a halogen, the substitution occurs at the alpha carbon position (i.e., the carbon immediately adjacent to the carbonyl group).

Preferred amino acid-based compounds of general formula (I) in accordance with the present invention for use in pharmaceutical antioxidant compositions in accordance with the invention include N-hydroxyethyl glycine ($HOCH_2CH_2NHCH_2C(O)OH$), which is also referred to herein as "monocine"; N,N-bis(hydroxyethyl)glycine ($(HOCH_2CH_2)_2NHCH_2C(O)OH$), which is also referred to herein as "bicine"; N-(bis-hydroxymethyl)methyl glycine ($(HOCH_2)_2CHNHCH_2C(O)OH$), which is also referred to herein as "dicine"; N-tris(hydroxymethyl)methyl glycine ($(HOCH_2)_3CNHCH_2C(O)OH$), which is also referred to herein as "tricine"; tricine thioethyl ester ($(HOCH_2)_3CNHCH_2C(O)SCH_2CH_3$); tricine ethyl ester ($(HOCH_2)_3CNHCH_2C(O)OCH_2CH_3$); tricine choroethyl ester ($(HOCH_2)_3CNHCH_2C(O)OCH_2CH_2Cl$); tricine trichloroethyl ester ($(HOCH_2)_3CNHCH_2C(O)OCH_2CCl_3$); tricine amide ($(HOCH_2)_3CNHCH_2C(O)NH_2$); tricine hydrazide ($(HOCH_2)_3CNHCH_2C(O)NHNH_2$); N-3-hydroxypropyl glycine ($HOCH_2CH_2CH_2NHCH_2C(O)OH$); N-2-hydroxypropyl glycine ($CH_3C(OH)HCH_2NHCH_2C(O)OH$); 2-carboxy-5-hydroxymethyl-pyrrolidine as in formula (II):

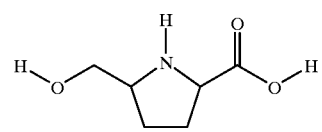

(II)

and 2-carboxy-6-hydroxymethyl-piperidine as in formula (III):

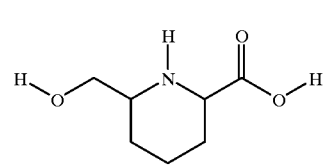

(III)

The above compounds in Formulas (II) and (III) may be prepared as in Example 1 herein. In addition, 2,6-dicarboethoxy-piperidine may also be prepared from the leaves of *Lobelia inflata* by oxidation with $CrO_3$ followed by ethyl esterification of the crude product with sulfuric acid and ethanol. The herb *Lobelia inflata* is an excellent source for the parent compound Norlobelanine (Merck Index 12$^{th}$ edition 1996, 6802). Alternatively, acylation of N-carbobenzoxy-pipecolic acid with ethyl formate followed by reduction of the resulting aldehyde and deprotection with hydrogen gas can afford 2-carboxy-5-hydroxymethyl pyrrolidine directly. The preparation of [afford] 2-carboxy-5-hydroxymethyl pyrrolidine may also be effected by alkylation of the dianion of N-carbobenzoxy-4-oxyproline with diethyl carbonate, prepared from 2 equivalents of lithium diisopropyl amide.

The most preferred amino acid-based compounds of general formula (I) in accordance with the present invention for use in pharmaceutical antioxidant compositions include bicine, tricine, derivatives thereof and mixtures thereof.

The present invention also encompasses the preparation and use of pharmaceutical antioxidant compositions, including therapeutic agents, medicaments and other related pharmaceutical compositions (referred to herein generally as "pharmaceutical antioxidant compositions"). Such compositions have low toxicity, high bioavailability and include an amino acid-based compound as an active ingredient having the general formula (I) as shown above, wherein A is represented by the formula:

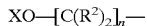

wherein n is preferably an integer of from 1 to about 3, X is selected from the group consisting of a hydrogen atom, an acyl group and a halogenated acyl group as described above, and each $R^2$ is independently selected from the group consisting of a hydrogen atom, an alkyl group having from 1 to about 3 carbon atoms and a hydroxyalkyl group having from 1 to about 3 carbon atoms, as well as $CH_2OX$ as described fully above. Z is also as described above and is selected from the group consisting of a hydrogen atom, an alkyl group of from 1 to about 3 carbon atoms and A. $R^1$ is an amino acid side chain group or an amino acid side chain group which forms with $R^2$ a single heterocyclic ring structure having a total of from 5 to 7 atoms as noted above. Q is preferably a substituent selected from the group consisting of a hydroxyl, $-N(R^2)_2$, $-NR_2(NR_2)_2$, $-SR^2$, an alkoxy, a halogenated alkoxy, an O-acyl and an O-alpha-halogenated acyl, as described fully above.

Such a pharmaceutical antioxidant composition may include the amino acid-based compound active ingredient alone, in a form suitable for administration to a subject mammal, or the antioxidant composition may include the active ingredient and one or more pharmaceutically acceptable carriers, one or more additional components including, for example additional antioxidants, binders, fillers, excipients, glidants and the like as described further below, or some combination of these. Suitable additional antioxidants for inclusion in the pharmaceutical antioxidant compositions in accordance with the present invention include, for example ω-3-unsaturated fatty acids, polyphenols, vitamin E, vitamin E derivatives, bioflavanoids and proanthocyanidins.

Preferred ω-3-unsaturated fatty acids for inclusion in a pharmaceutical antioxidant composition in accordance with the present invention are docosahexaenoic acid (DHA) and eicosapentaenoic acid (EPA). However, it will be understood, based on this disclosure, that any fatty acid possessing an unsaturated carbon chain and which has known antioxidant properties can be included in pharmaceutical antioxidant compositions in accordance with the present invention. Similarly, any polyphenol, vitamin or vitamin derivative, bioflavonoid or proanthocyanidin having known antioxidant properties can be included in pharmaceutical antioxidant compositions in accordance with the present invention. For example, vitamins C and E, DHA and EPA are preferred optional additives.

Amino acid-based compounds of general formula (I) for inclusion in pharmaceutical antioxidant compositions in accordance with the present invention can be obtained commercially, synthesized from commercially obtainable starting materials or derived from one or more natural sources. For example, tricine is commercially available in a physiologically acceptable form from at least Sigma Chemical Co., St. Louis, Mo., and Mallinkrodt Chemical Co., Phillipsburg, N.J.

Additionally, amino acid-based compounds of general formula (I) for inclusion in pharmaceutical antioxidant compositions in accordance with the present invention can be prepared by reacting a halogenated acetic acid with an aminoalkanol. For example, N-3-hydroxypropyl glycine can be prepared by heating chloroacetic acid with excess 3-aminopropanol according to the following reaction:

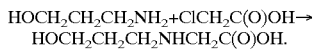

Preferably the reaction occurs at about 65° C. Other amino acid-based compounds can be prepared using halogenated acetic acid analogs wherein the halogen-bearing carbon is further substituted with an amino acid side chain group. For example, alanine-based compounds can be prepared by reacting 2-chloropropanoic acid ($CH_3CH_2ClC(O)OH$) with an aminoalkanol.

Alternatively, certain amino acid-based compounds of general formula (I) for inclusion in pharmaceutical antioxidant compositions in accordance with the present invention such as glycine-based compounds can be prepared by the reductive amination of an aminoalkanol and glyoxalic acid in the presence of a reducing agent such as sodium cyanoborohydride.

Also, amino acid-based compounds of general formula (I) for inclusion in pharmaceutical antioxidant compositions in accordance with the present invention can be derived from natural sources. Seaweeds (macroalgae) especially of the brown variety known botanically as Phaeophyceae contain certain amino acid-based compounds of general formula (I), for example, monocine. Thus, amino acid-based compounds can be extracted from brown macroalgae which contain amino acid-based compounds of general formula (I) including, for example: *Petalonia fascia, Fucus fascia, Ilea fascia, Phyllitis fascia, Phyllitis debilis, Scytosiphon fascia, Laminara fascia, Ectocarpus acutus, Alaria esceulenta, Fucus esculentus, Alaria platyrhiza,* Dabberlocks (Scotland), Daberlocks, Babberlocks, Bladder locks, *Essbarer riementang, Alimentaire varech, Edible fucus, Edible kelp* and *Scytosiphon dotyi.* Extraction can be accomplished by any known means such as freeze-drying, distillation, solvent extraction, or any suitable means later developed. The preferred extraction process involves extraction of dried harvested algae leaves with hot water, followed by concentration to between about ¼ and ⅒ of the amount by volume. Isolation of amino acids after filtration of solids may be accomplished by precipitation with ethanol solvent or by evaporation of water.

Other amino acid-based compounds of general formula (I) wherein Q is a substituent selected from the group consisting of hydroxy, $-N(R^2)_2$, $-NR^2(NR^2)_2$, $-SR^2$, an alkoxy, a halogenated alkoxy, an O-acyl or an O-halogenated acyl can be prepared by conventional derivatization reactions using compounds prepared in accordance with the methods described above or those which have been obtained commercially or through extraction from natural sources. It will be understood, based on this disclosure, that one of ordinary skill in the art may use other typical organic and natural syntheses of these compounds to form the compounds of the invention and their derivatives without departing from the spirit and scope of this invention.

Amino acid-based compounds of the general formula (I) in accordance with the present invention are capable of forming a stabilized nitroxyl radical, as shown below, upon oxidation of the secondary amino functionality.

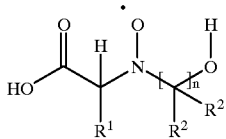

While not wishing to be bound by theory, it is believed that at least part of the ability of the amino acid-based compounds of the general formula (I) to function effectively as antioxidants is a result of the stabilization of the nitroxyl radical which results from oxidation of the amino acid-based compounds. The stabilization is believed to be due to the proximity of both the carbonyl oxygen atom and the at least one hydroxyl moiety adjacent to the secondary nitrogen atom.

For example, tricine forms a stabilized nitroxyl radical, represented by the following formula upon oxidation.

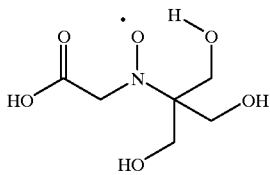

Again, while not wishing to be bound by theory, it is believed that the interatomic distance between the oxygen the carbonyl group and the hydrogen atom of the adjacent hydroxyl group provides stabilizing forces. Thus, as would be understood by one of ordinary skill in the art, amino acid-based compounds of the general formula (I) in accordance with the present invention, will offer similar antioxidant properties due to the particular proximity of the carbonyl group and the presence of an adjacent hydroxyl group, preferably when n is 2 in formula (I) above.

Amino acid-based compounds of the general formula (I) for use in pharmaceutical antioxidant compositions in accordance with the present invention exhibit low toxicity. It is essential that any amino-acid-based compound used in accordance with the present invention have a low toxicity such that internal use in humans and other mammals is safe and well tolerated. Amino acid-based compounds used in accordance with the invention generally display no acute toxic effects at 1000 mg/Kg in rats after 2 weeks following oral administration. Preferably, amino acid-based compounds used in accordance with the present invention will display no effects at oral doses of at least 2000 mg/Kg in rats. While certain amino-acid-based compounds used in accordance with the present invention have been shown to have, or are known to have the requisite general low toxicity in accordance with the present invention, one of ordinary skill in the art will understand, based on this disclosure as set forth herein and further below, that other amino acid-based compounds can be tested to determine their respective toxicity level. For example, a cohort of rats can be fed a given dosage of an amino acid-based compound of general formula (I) and the relative toxic effects of the cohort can be monitored in comparison to a cohort fed a normal diet using standard EPA protocols.

Amino acid-based compounds of the general formula (I) for use in pharmaceutical antioxidant compositions in accordance with the present invention exhibit high bioavailability. It is essential to the performance of a pharmaceutical antioxidant composition in accordance with the present invention that the amino acid-based compound of the general formula (I) incorporated therein have a high bioavailability. At neutral pH values, the acid-based compounds of the general formula (I) exist in a zwitterionic form which provides a high degree of aqueous solubility. Furthermore, the amino acid-based compounds of the general formula (I) are stable to both the highly acidic conditions and enzyme digestion typical of the body's gastric fluids and metabolism. Their relatively low molecular weight and small molecular size in contrast to a much larger peptide or protein, provide a means for passage into circulation where local concentration of an antioxidant pharmaceutical composition is necessary to support their protective effect. Amino acid-based compounds used in accordance with the present invention possess oral bioavailability, because they are soluble in aqueous body fluids, stable to the harsh environment of the gastrointestinal tract, and of appropriate size to gain access to the circulation compartment prior to clearance by a metabolic pathway.

The combination of low-toxicity, high-bioavailability and the ability to support a stable nitroxyl radical intermediate provide amino acid-based compounds for incorporation into pharmaceutical antioxidant compositions that are thus highly effective and relatively safe for administration to a subject in treating or preventing antioxidant responsive diseases.

Administration of a pharmaceutical antioxidant composition to a subject in accordance with the method of the present invention can be useful for treating and/or preventing antioxidant responsive diseases in the subject, as described elsewhere in the present disclosure. The amino acid-based compound active ingredient may be present in the pharmaceutical antioxidant composition in the form of a physiologically acceptable salt, such as in combination with a physiologically acceptable cation or anion, as is well known in the art.

As used herein, the term "pharmaceutically acceptable carrier" means a chemical composition with which the active ingredient may be combined and which, following the combination, can be used to administer the active ingredient to a subject.

As used herein, the term "physiologically acceptable" salt means a salt form of the active ingredient which is compatible with any other ingredients of the pharmaceutical antioxidant composition and which is not deleterious to the subject to which the composition is to be administered.

The formulations of the pharmaceutical antioxidant compositions described herein may be prepared by any method known or hereafter developed. In general, such preparatory methods include the step of bringing the active ingredient into association with a carrier or one or more other additional components, and then, if necessary or desirable, shaping or packaging the product into a desired single- or multi-dose unit.

Although the descriptions of pharmaceutical antioxidant compositions provided herein are principally directed to pharmaceutical antioxidant compositions which are suitable for ethical administration to humans, it will be understood by the skilled artisan, based on this disclosure, that such compositions are generally suitable for administration to any mammal. Modification of pharmaceutical antioxidant compositions suitable for administration to humans in order to render the compositions suitable for administration to various animals is well understood, and the ordinarily skilled veterinary pharmacologist can design and perform such modification with routine experimentation, if any. Subjects to which administration of the pharmaceutical antioxidant compositions of the invention is contemplated include, but are not limited to, humans and other primates, mammals including commercially relevant mammals such as cattle, pigs, horses, sheep, cats, and dogs, birds including commercially relevant birds such as chickens, ducks, geese, and turkeys, fish including farm-raised fish and aquarium fish, and crustaceans such as farm-raised shellfish.

Pharmaceutical antioxidant compositions that are useful in the methods of the invention may be prepared, packaged, or sold in formulations suitable for oral, parenteral and topical administration. Other contemplated formulations include projected nanoparticles, liposomal preparations, resealed erythrocytes containing the active ingredient, and immunologically-based formulations.

A pharmaceutical antioxidant composition of the invention may be prepared, packaged, or sold in bulk, as a single unit dose, or as a plurality of single unit doses. As used herein, a "unit dose" is a discrete amount of the pharmaceutical antioxidant composition comprising a predetermined amount of the amino acid-based compound active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional components in a pharmaceutical antioxidant composition of the invention will vary, depending upon the identity, size, and condition of the subject treated and further depending upon the route by which the composition is to be administered. By way of example, the composition may comprise between 0.1% and 100% by weight of the active ingredient based on the total weight of the composition. In addition to the active ingredient, a pharmaceutical antioxidant composition of the invention may further comprise one or more additional antioxidants, as described above.

Controlled- or sustained-release formulations of a pharmaceutical antioxidant composition of the invention may be made using conventional technology.

A formulation of a pharmaceutical antioxidant composition of the invention suitable for oral administration may be prepared, packaged, or sold in the form of a discrete solid dosage unit including, but not limited to, a tablet, caplet, a hard or soft capsule, a cachet, a troche, or a lozenge, each containing a predetermined amount of the active ingredient. Other formulations suitable for administration include, but are not limited to, a powdered or granular formulation, an aqueous or oily suspension, an aqueous or oily solution, or an emulsion.

As used herein, an "oily" liquid is one which comprises a carbon-containing liquid molecule and which exhibits a less polar character than water.

A tablet comprising the active ingredient may, for example, be made by compressing or molding the active ingredient, optionally with one or more additional components. Compressed tablets may be prepared by compressing, in a suitable device, the active ingredient in a free-flowing form such as a powder or granular preparation, optionally mixed with one or more of a binder, a lubricant, a glidant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycolate. Known surface active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc. While these components have been listed, it will be understood based on this disclosure that other similar additional components which are known or which are to be developed may be included in the compositions of the invention.

Tablets may be non-coated or they may be coated using known methods or methods to be developed to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically-controlled release tablets. Tablets may further comprise a sweetening agent, a flavoring agent, a coloring agent, a preservative, or some combination of these in order to provide pharmaceutically elegant and palatable preparation.

Hard capsules comprising the active ingredient may be made using a physiologically degradable composition, such as gelatin. Such hard capsules comprise the active ingredient, and may further comprise additional components including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

Oral compositions may be made, using known technology or technology to be developed, which specifically release orally-administered agents in the small or large intestines of a human patient. For example, formulations for delivery to the gastrointestinal system, including the colon, include enteric coated systems, based, e.g., on methacrylate copolymers such as poly(methacrylic acid, methyl methacrylate), which are only soluble at pH 6 and above, so that the polymer only begins to dissolve on entry into the small intestine. The site where such polymer formulations disintegrate is dependent on the rate of intestinal transit and the amount of polymer present. For example, a relatively thick polymer coating is used for delivery to the proximal colon (Hardy et al., 1987 Aliment. Pharmacol. Therap. 1:273–280). Polymers capable of providing site-specific colonic delivery can also be used, wherein the polymer relies on the bacterial flora of the large bowel to provide enzymatic degradation of the polymer coat and hence release of the drug. For example, azopolymers (U.S. Pat. No. 4,663,308), glycosides (Friend et al., 1984, J. Med. Chem. 27:261–268) and a variety of naturally available and modified polysaccharides (PCT GB 89/00581) may be used in such formulations.

Pulsed release technology such as that described in U.S. Pat. No. 4,777,049 may also be used to administer the active agent to a specific location within the gastrointestinal tract. Such systems permit drug delivery at a predetermined time and can be used to deliver the active agent, optionally together with other additives that may alter the local microenvironment to promote agent stability and uptake, directly to the colon, without relying on external conditions other than the presence of water to provide in vivo release.

Liquid formulations of a pharmaceutical antioxidant composition of the invention which are suitable for administration may be prepared, packaged, and sold either in liquid form or in the form of a dry product intended for reconstitution with water or another suitable vehicle prior to use.

Liquid suspensions may be prepared using conventional methods or methods to be developed to achieve suspension of the active ingredient in an aqueous or oily vehicle. Aqueous vehicles include, for example, water and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional components including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g. polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin and acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol. While such components are listed as exemplary components, it will be understood based on this disclosure that other similar components or components to be developed for such liquid suspensions may be used within the scope of the invention.

Liquid solutions of the active ingredient in aqueous or oily solvents may be prepared in substantially the same manner as liquid suspensions, the primary difference being that the active ingredient is dissolved, rather than suspended in the solvent. Liquid solutions of the pharmaceutical antioxidant composition of the invention may comprise each of the components described with regard to liquid suspensions, it being understood that suspending agents will not necessarily aid dissolution of the active ingredient in the solvent. Aqueous solvents include, for example, water and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of an antioxidant preparation of the invention may be prepared using known methods or methods to be developed. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical antioxidant composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional components including, for example, sweetening or flavoring agents.

As used herein, "additional components" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; pharmaceutically acceptable polymeric or hydrophobic materials as well as other components which are described, for example, in Genaro, ed., 1985, *Remington's Pharmaceutical Sciences,* Mack Publishing Co., Easton, Pa., which is incorporated herein by reference.

A pharmaceutical antioxidant composition of the invention may be administered to deliver a dose of between 1 ng/kg/day and 100 mg/kg/day, and preferably to deliver of between from about 0.1 mg/kg/day to about 100 mg/kg/day of the active ingredient, and preferably comprises from about 3 mg/kg/day to about 30 mg/kg/day of the active ingredient. It is understood that the ordinarily skilled physician or veterinarian will readily determine and prescribe a therapeutically effective amount of the compound to treat, delay the onset of and/or prevent antioxidant responsive diseases in the subject. In so proceeding, the physician or veterinarian may, for example, prescribe a relatively low dose at first, subsequently increasing the dose until an appropriate response is obtained. It is further understood, however, that the specific dose level for any particular subject will depend upon a variety of factors including the activity of the specific compound employed, the age, body weight, general health, gender, and diet of the subject, the time of administration, the route of administration, the rate of excretion, any drug combination, and the severity of the antioxidant responsive disease being treated or prevented. Thus, a "therapeutically effective amount" of an amino acid-based compound of the general formula (I) may vary but can be determined by those of ordinary skill in the art with minimal testing.

As discussed above, the present invention includes a method of treating, delaying the onset of and/or preventing antioxidant-responsive diseases in mammals, said method comprising administering a pharmaceutical antioxidant composition comprising a therapeutically effective amount of an amino acid-based compound of the general formula (I). As used herein, "antioxidant responsive diseases" refers to any physiological condition, ailment, disorder, or disease of the subject mammal, a cause of which is or is believed to be oxidative stress upon or within the subject. For example, antioxidant responsive diseases include atherosclerosis, coronary artery disease, restenosis, reperfusion injury such as following ischemia caused, for example by blood clots, organic repair or transplant surgery, osteoarthritis, neurodegenerative disorders such as Parkinson's disease and Alzheimer's disease, as well as stroke. Thus, the present invention contemplates a method of treating, delaying the onset of and/or preventing each of these diseases, said method comprising administering a pharmaceutical antioxidant composition comprising a therapeutically effective amount of an amino acid-based compound of the general formula (I).

It is known to those of ordinary skill in the art that many diseases, including those listed above, have been identified as being caused, initiated or amplified, at least in part, by physiological oxidation. For example, in U.S. Pat. Nos. 5,750,351; 5,773,209; 5,773,231; 5,792,787; 5,783,596; 5,807,884; 5,811,449; 5,821,260; and 5,846,959, which are each hereby incorporated by reference, the oxidation of low density lipoproteins (LDL's) within the body is described as the central event that initiates and propagates atherosclerosis, and antioxidant therapy is described as a treatment for atherosclerosis and other coronary artery diseases. In Yamaguchi, Y., et al., "Enhancement of Aortic Cholesterol Deposition by Dietary Linoleic Acid in Cholesterol-Fed Mice: An Animal Model for Primary Screening of Antiatherosclerosis Agents", *J. Pharmaceutical and Toxicological Methods,* Vol. 30(3), pp.169–175 (November 1993), the entire contents of which are herein incorporated by reference, the examination of the aorta after ingestion of high cholesterol diets with and without antioxidants is an effective evaluation for the efficacy of antioxidants in preventing and treating atherosclerosis.

Restenosis is a complication of coronary angioplasty and proceeds by proliferation of vascular smooth muscle cells to close an artery. Vascular smooth muscle cell proliferation is stimulated by apoptosis, a programmed cell death, which in turn, is stimulated by oxidation induced release of protein kinases. This cascade effect lends itself to regulation with antioxidant treatment and is a known indication of pharmaceutical antioxidants including those of the present invention. For example, U.S. Pat. No. 5,326,757 describes an antioxidant composition based upon administration of antioxidant vitamins C and E in conjunction with glutathione.

Damage associated with reperfusion injury, while dependent upon the length of anoxia, is widely believed to be due to the sudden perfusion of oxygen leading to the generation of reactive oxygen species at the site of the eventual damage. For example, U.S. Pat. Nos. 5,506,266 and 5,080,886, herein incorporated by reference, both describe a similar connection between tissue damage due to reperfusion and oxidation. Simpson, P., et al., "Free Radicals and Myocardial Ischemia and Reperfusion Injury", *J. Lab. Clin. Med.,* Vol. 110(1), pp. 13–30 (July 1987), also incorporated herein by reference, describes the growing body of evidence for the connection between oxidation and reperfusion injury. The connection is strengthened upon the combined observations of locomotor behavioral changes with histological evidence for neuronal destruction upon reperfusion. In an effective animal model for stroke, A. Hunter et al., "Animal Models of Acute Ischemic Stroke: Can They Predict Clinically Successful Neuroprotective Drugs?," Trends in the Pharmaceutical Sciences, 16, 123 (1995) reviews the extent of the utility of using Mongolian gerbils to access pharmaceuticals. In accordance with the method of the present invention, and the data presented in the examples, neuronal damage caused by stroke can be reduced or prevented via the administration of antioxidant compositions of the invention and in accordance with the method of the present invention.

An analogous process occurs to organs undergoing transplant. In order to minimize nonfunctioning grafts and organ rejection, antioxidant pharmaceutical compositions protect the harvested organ during transportation and storage from the injuries induced upon reperfusion. For example, U.S. Pat. No. 5,756,492 describes the connection between oxidation and successful methods for graft survival.

Antioxidant pharmaceutical compositions of formula (I) are also effective for treating arthritis. The presence of oxidized substrates in the plasma of arthritis patients was identified to be related to patients suffering from rheumatoid arthritis by H. Oztruk, in "Oxidant/Antioxidant Status of Plasma Samples from Patients with Rheumatoid Arthritis," Rheumatology International, 19, 35–37 (1999). Clearly, the relationship between reactive oxygen species and cytokine activation was also verified in a publication on the pathology of arthritis and cancer by Lo, "Reactive Oxygen Species Mediate Cytokine Activation of c-Jun $NH_2$-Terminal Kinases," J. Biological Chemistry, 271, 15703 (1996). Antioxidants have also been described as effective in treating inflammatory ailments. See Della Valle, U.S. Pat. No. 5,480, 645, incorporated herein by reference, which correlates many oxidation initiated inflammatory diseases, including arthritis and PCT Publication WO97/41487 which also describes this correlation and is also incorporated herein by reference. Thus, it would be expected, based on this disclosure, that the compounds of the invention and the method of the invention as well as the pharmaceutical antioxidant compositions of the invention will delay the onset of, treat and/or prevent the debilitating effects of inflammatory ailments such as arthritis.

The use of antioxidant compositions in treating and preventing neurodegenerative disorders is well documented. For example, U.S. Pat. No. 5,874,468 describes the treatment of Parkinson's disease, Alzheimer's disease and Creutzfeldt-Jakob's disease via the administration of antioxidant compounds. Additionally, de Rijk, M., et al., "Dietary Antioxidants and Parkinson Disease", *Arch. Neurol.,* Vol. 54, pp. 762–5 (June 1997); Rawls, R., "When Neurons Go Awry", *Chemical & Engineering News,* (Sep. 21, 1998); Shoulson, I., "Experimental Therapeutics of Neurodegenerative Disorders: Unmet Needs", *Science,* Vol. 282, pp.1072–4 (Nov. 6, 1998); and Pitchumoni, S, et al., "Current Status of Antioxidant Therapy for Alzheimer's Disease", *J. Amer. Geriatrics Society,* Vol. 46(12), pp. 1566–72 (December 1998); all describe the correlation between neurodegenerative disorders and oxidative damage, and further describe the effective treatment of such disorders via administration of antioxidant compounds.

Finally, in accordance with the method of the present invention, the neuronal damage caused by stroke can be reduced or prevented via the administration of pharmaceutical antioxidant compositions in accordance with the present invention.

It will be understood by one of ordinary skill in the art, based on this disclosure, that an amino acid-based compound of the general formula (I), for incorporation in a pharmaceutical antioxidant composition in accordance with the present invention, which exhibits antioxidant properties when evaluated with respect to its ability to prevent or treat one antioxidant-responsive disease will be similarly effective in preventing or treating another antioxidant-responsive disease.

The present invention will now be described in further detail with reference to the following non-limiting examples.

EXAMPLE 1

Formation of 2-carboxy-5-hydroxymethylpyrrolidine and 2-carboxy-5-hydroxymethylpiperidine is undertaken by using the corresponding diesters of these compounds and reducing them with lithium aluminum hydride in cold diethyl ether followed by workup with aqueous acid, and filtration of the lithium salts and chromatography over silica gel. Specifically, a solution of lithium aluminum hydride in ether (18.4 mL, 1.0 M solution) is added dropwise to a $-78°$ C. solution of 2,6-dicarboethoxypiperazine (4 g) in anhydrous diethyl ether (400 mL) under a nitrogen atmosphere. The solution is allowed to warm slowly to room temperature with stirring under nitrogen, with stirring continuing for an additional 6 hours. The reaction is quenched upon dropwise addition of aqueous HCl (0.5mL, 0.1M) and should be stirred for an additional 2 hours. The aluminum salts are then filtered and the product solution concentrated under reduced pressure to a volume of 15 mL and for application to a bed of a silica gel column packed in hexane containing 20% diethyl ether. The product is eluted with 50% diethyl ether and 2-carboxy-5-hydroxymethylpiperidine-rich fractions are then combined. Evaporation of the combined fractions affords 2-carboxy-5-hydroxymethylpiperidine. 2-Carboxy-5-hydroxymethylpyrrolidine is prepared the same way from 2,5-carboethyoxypyrrolidine.

EXAMPLE 2

Tricine ethyl ester is prepared by mixing a 500 ml of a suspension of tricine 0.5 g/ml in ethanol with 1 ml of concentrated sulfuric acid. Subsequent distillation of the ethanol water azeotrope forms the ester.

EXAMPLE 3

Two cohorts of rats, each consisting of five females and five males, were marked and weighed. Each rat in a single cohort was administered 2000 mg/kg of tricine in a single oral dosage. Survival and body weight of the rats in each cohort was evaluated after 14 days to determine relative acute toxicity. Survival and general pathology was identical for both the control cohort and the tricine-treated cohort. These results indicate a preliminary acute toxicity level of tricine in rats of greater than approximately 2000 mg/kg.

EXAMPLE 4
Antioxidant Effectiveness by Competitive Inhibition of LDL Autoxidation The antioxidant performance of test compounds was evaluated by measuring the extent of low density lipoprotein hydroxyperoxide by copper catalyzed autoxidation using a published dye based color assay (FOX Assay, see Zadeh, "Methods in Enzymology", 300, 58 (1999)). The assay is easily performed and read in a 96-well microtitre plate. Microtitre plate readers assure rapid measurement of optical density which gives precise replicate measurements. Samples are evaluated in duplicate of triplicate (n=2 or n=3) with FOX reagent to indicate the level of LDL-hydroperoxide formed. Samples containing only LDL and copper sulfate without test materials, served as a positive control for comparison with identical mixtures containing test materials (Tables 1–6). Inhibition is characterized by a lower optical density than that obtained without test materials (LDL and copper sulfate alone).

Briefly, the procedure involved mixing human Low Density Lipoprotein (Sigma Chemical Company L2139) at a concentration of between 200–1000 $\mu$g/mL in phosphate buffered saline pH–7.4 (Pierce #28372 BupH™ with copper sulfate to a final concentration of 10 $\mu$g/mL. Incubation at 25° C. or 37° C., open to air effected oxidation, the mixture was sampled at time zero and between 3 and 20 hours of incubation for measurement of hydroperoxide in the FOX assay. Samples 25–30 $\mu$L were diluted with 10 volumes of FOX reagent (ferrous ammonium sulfate and xylene cyanol, see Zadeh, noted above) and allowed to stand for 30 minutes. Thereafter they were read in a microtitre plate reader. The average of duplicate or triplicate wells is tabulated in tables 1–6.

The inhibition of LDL oxidation by tricine, bicine, monocine, vitamin E, glycine-glycine (Good's buffer compound XIV) and seaweed extract was studied in the procedure above. Using the spectrophotometric technique known as the FOX assay, as described in Jiang, Z., et al., "Ferrous Ion Oxidation in Presence of Xylenol Orange for Detection of Lipid Hydroperoxide in Low Density Lipoprotein", *Analytical Biochemistry*, Vol. 202, pp. 384–9 (1992), the oxidation of LDL's in the presence of known hydroxyl radical scavengers (vitamin E and Good's buffer glycine-glycine), and in the presence of therapeutic agents in accordance with the present invention (tricine, bicine, seaweed extract), was monitored. Table 1 shows the tricine inhibition of LDL oxidation (concentration dependence), using the FOX assay OD average of triplicate determinations at room temperature. Table 2, below, shows the bicine inhibition of LDL oxidation (concentration dependence), using FOX assay OD average of triplicate determinations after 4 hours at room temperature. Table 3 shows the comparison of hydroxyalkyl amino acid to a Good's Buffer which demonstrates that this is not simply a buffering effect and uses the FOX assay OD average of triplicate determinations after 4 hours at room temperature. Norman Good et al., "Hydrogen Ion Buffers For Biological Research," *Biochemistry*, vol. 5, p. 467 (1966). Table 4 below shows the seaweed extract and hydroyalkyl glycines comparison (LDL oxidation) using the FOX assay OD average of triplicate determinations after 3 hours at room temperature. Table 5 below shows a comparison of tricine, bicine and monocine oxidation inhibition of LDL at 37° C., average n=3 with standard deviation. Table 6 is a comparison of tricine, bicine, monocine and vitamin E oxidation inhibition of LDL at 37° C., average n=3 measurement with standard deviation.

TABLE 1

| Time (hours) | Sample | None | Tricine 25 $\mu$M | Tricine 50 $\mu$M | Tricine 100 $\mu$M |
|---|---|---|---|---|---|
| 0 | average n = 3 | (0) | −0.012 | −0.007 | 0.0645 |
|  | (std. deviation) | (0) | (0) | (0.004) | (0.095) |

TABLE 1-continued

| Time (hours) | Sample | None | Tricine 25 μM | Tricine 50 μM | Tricine 100 μM |
|---|---|---|---|---|---|
| 4 | average n = 3 | 0.295 | 0.061 | 0.038 | 0.028 |
|   | (std. deviation) | (0.021) | (0.009) | (0.067) | (0.005) |

TABLE 2

| Time (hours) | Sample | none | Bicine 25 μM | Bicine 50 μM | Bicine 100#M |
|---|---|---|---|---|---|
| 0 | average n = 3 | 0 | −0.010 | −0.007 | −0.002 |
|   | (std. deviation) | (0) | (0.005) | (0.016) | (0.001) |
| 4 | average n = 3 | 0.295 | 0.050 | 0.030 | 9.040 |
|   | (std. deviation) | (0.021) | (0.012) | (0.011) | (0.009) |

TABLE 3

| Time (hours) | Sample | none | Bicine 25 μM | Tricine 25 μM | Gly-Gly[1] 25 μM |
|---|---|---|---|---|---|
| 0 | average n = 3 | 0 | −0.012 | −0.0095 | −0.006 |
|   | (std. deviation) | (0) | (−0.012) | (0.005) | (0.001) |
| 4 | average n = 3 | 0.295 | 0.061 | 0.050 | 0.104 |
|   | (std. deviation) | (0.021) | (0.009) | (0.012) | (0.001) |

[1]Gly-Gly is glycylglycine, see, Good at al, noted above, compound XIV table page 472.

TABLE 4

| Time (hours) | None | Tricine 50 μM | Bicine 50 μM | Alaria Esculenta Extract |
|---|---|---|---|---|
| 0 | 0 | 0.005 | 0.008 | −0.032 |
| 3 | 0.292 | 0.058 | 0.027 | 0.012 |

TABLE 5

| Time (hours) | None | Tricine (10 mM) | Bicine (10 mM) | Monocine (10 mM) |
|---|---|---|---|---|
| 0 | 0.03 | −0.01 | −0.02 | −0.04 |
| (std. deviation) | (0.04) | (0.04) | (0.02) | (0.02) |
| 3 | 0.99 | 0.05 | 0.02 | 0.05 |
| (std. deviation) | (0.06) | (0.04) | (0.04) | (0.04) |

TABLE 6

| Time (hours) | None | Tricine (0.5 mM) | Bicine (0.5 mM) | Monocine (0.5 mM) | Vitamin E (0.5 mM) |
|---|---|---|---|---|---|
| 0 | 0.058 | 0.038 | 0.027 | 0.053 | 0.144 |
| (std. deviation) | (0.046) | (0.045). | (0.069) | (0.039) | (0.039) |
| 3 | 0.706 | 0.189 | 0.133 | 0.703 | 1.008 |
| (std. deviation) | (0.091) | (0.065) | (0.036) | (0.075) | (0.076) |

EXAMPLE 5

Ten female new Zealand white rabbits were divided into two groups of five (5) rabbits and subjected to an identical diet of Purina® rabbit chow supplemented with 1% cholesterol. One group of five rabbits did not receive test article in their drinking water and served as a control group. A second group of five (5) rabbits received 1% tricine in their drinking water. Both groups were maintained under this feeding protocol for a period of twelve (12) weeks. Plasma samples were taken at study initiation and at two (2) week intervals throughout the study for measurement of total cholesterol. Systemic observations and body weights were regularly recorded. At twelve (12) weeks, the thoracic aorta was harvested from each animal, sliced longitudinally and preserved in 10% neutral formalin for subsequent analysis.

Each aorta was individually stained with Sudan IV, and photographed for the extent of atherosclerotic lesions. Comparisons of percent atheroscledrotic lesions on the luminal surface between the groups enabled evaluation of the effect of tricine test article on atherosclerosis in this rabbit model. The results shown below in Table 7, demonstrate 63% reduced plaque deposits in the aorta of tricine treated rabbits.

TABLE 7

| Rabbit ID No. | Arch Area | Descending Area | Total Area |
|---|---|---|---|
| Control Group | | | |
| F1916 | 38 | 42 | 39 |
| F1917 | 39 | 35 | 37 |
| F1918 | 80 | 93 | 88 |
| F1919 | 65 | 68 | 67 |
| F1920 | 93 | 88 | 92 |
| Mean Value | 63 | 65 | 65 |
| Median Value | 65 | 68 | 67 |
| Standard Deviation (±) | 24.5 | 26.2 | 26.1 |
| 95% Confidence Interval (±) | 21 | 21 | 21 |
| 1% Tricine Ingestion | | | |
| F1909 | 19 | 21 | 20 |
| F1911 | 39 | 28 | 38 |
| F1912 | 27 | 21 | 26 |
| F1914 | 17 | 8 | 14 |
| F1915 | 22 | 17 | 21 |
| Mean Value | 25 | 19 | 24 |
| Median Value | 22 | 21 | 21 |
| Standard Deviati6n (±) | 8.8 | 7.3 | 9.0 |
| 95% Confidence Interval (±) | 8 | 6 | 8 |

EXAMPLE 6

Mongolian gerbils are subjected to bilaterial occlusion of carotid arteries to cause complete forebrain ischemia. The Mongolian gerbil is extensively used as a model of cerebral ischemia because of its unusual cerebral circulation resulting in sensitive and pronounced destruction of hippocampal neuron cells. as a result, bilateral occlusion of carotid arteries causes complete forebrain ischemia. The gerbils were divided into three groups, Group 1 gerbils were sham control and were administered vehicle (control) orally without carotid occlusion. Group 2 received oral tricine treatment at 2000 mg/Kg in vehicle solution both 60 minutes before and after carotid occlusion. Group 7 gerbils received vehicle (control) 60 minutes before and after occlusion. The arteries were occluded after a midline cervical incision was made to expose both common carotid arteries. The surgery was performed on a heated surface to maintain body temperature. On completion of surgery, the animals were placed on Vetbed® and allowed to recover under a heat lamp. (Group 1) was subjected to the same surgical procedures except that the carotid arteries were not occluded. The day of surgery is identified as Day 1.

Locomotor Activity Measurement

At approximately 96 hours after surgery, animals were tested for changes in locomotor activity, over two (2) consecutive periods of 15 minutes, using an automated cage. The automated cages contained photoactivated beams at two (2) positions (a low height and a high height) that recorded the number of crossings each gerbil made in each of two consecutive 15 minute periods.

Termination and Histology

Animals were killed on day 5, after completion of locomotor testing, by overdose with anaesthetic and perfusion with saline followed by a solution containing 10% neutral buffered formalin to fix the brain in situ. The brains were removed by dissection, 5 μm sections were taken at the level of the dorsal hippocampus, to coincide with $CA_1$ area, and stained with haematoxylin and eosin. the sections were examined under light microscope, rated for severity of neuronal damage to the $CA_1$ area.

Data from the histological evalution of hippcampal neurons are set forth in Tables 8 and 9. Data from each gerbil's locomotor activity measurements are set forth in Tables 10–12 below.

In Tables 8 and 9 the following apply:

0=Normal→no apparent neuronal damage

1=Minimal→up to approximately 25% of neurons damaged

2=Moderate→approximately 25% to 75% of neurons damaged

3=Marked→approximately 75% to 100% of neurons damaged

4=Severe→approximately 100% of neurons damaged, with permanent gliosis and possible damage in the $CA_2$ and $CA_3$ regions

TABLE 8

| Gerbil Group No. | Individual Gerbil No. | Side 1 Rating | Side 2 Rating | Total Rating |
|---|---|---|---|---|
| 1 | 1 | 0 | 0 | 0 |
|   | 2 | 0 | 0 | 0 |
|   | 3 | 0 | 0 | 0 |
|   | 4 | 0 | 0 | 0 |
|   | 5 | 0 | 0 | 0 |
|   | 8 | 0 | 0 | 0 |
|   | 9 | 0 | 0 | 0 |
|   | 10 | 0 | 0 | 0 |
|   | 77 | 0 | 0 | 0 |
| 3 | 22 | 3 | 3 | 6 |
|   | 23 | 1 | 1 | 2 |
|   | 25 | 1 | 0 | 1 |
|   | 26 | 1 | 1 | 2 |
|   | 28 | 1 | 1 | 2 |
|   | 29 | 1 | 1 | 2 |
| 7 | 6 | 1 | 1 | 2 |
|   | 75 | 3 | 2 | 5 |
|   | 76 | 3 | 3 | 6 |

TABLE 9

| Gerbil Group No. | Total Number of Animals Examined | Total Score for Group | Mean Score for Group |
|---|---|---|---|
| 1 | 9 | 0 | 0 |
| 3 | 6 | 15 | 2.5 |
| 7 | 3 | 13 | 4.3 |

As can be seen from the data set forth in Tables 8 and 9, gerbils which receive the diet supplemented with a pharmaceutical antioxidant composition in accordance with the present invention suffered little or no damage from the stroke. Table 10 set forth below demonstrates the negative control gerbils' locomotor activity for the gerbils in Group 1.

TABLE 10

| Animal Number | Beam level | Time 15 min. | Time 30 min. | Total |
|---|---|---|---|---|
| 1 | High | 78 | 14 | 92 |
|   | Low | 298 | 104 | 402 |
| 2 | High | 46 | 15 | 61 |
|   | Low | 407 | 77 | 484 |
| 3 | High | 52 | 37 | 89 |
|   | Low | 245 | 131 | 376 |
| 4 | High | 55 | 35 | 90 |
|   | Low | 374 | 128 | 502 |
| 5 | High | 74 | 42 | 116 |
|   | Low | 426 | 207 | 633 |
| 8 | High | 77 | 14 | 91 |
|   | Low | 312 | 71 | 383 |
| 9 | High | 62 | 13 | 75 |
|   | Low | 460 | 101 | 561 |
| 10 | High | 74 | 23 | 97 |
|   | Low | 282 | 91 | 373 |
| 77 | High | 40 | 12 | 52 |
|   | Low | 275 | 51 | 326 |

Table 11 sets forth the results for the Tricine treated gerbils in Group 3 with respect to their locomotor activity.

TABLE 11

| Animal Number | Beam Level | Time (15 min) | Time (30 min) | Total |
|---|---|---|---|---|
| 22 | High | 55 | 16 | 7.1 |
|   | Low | 543 | 184 | 727 |
| 23 | High | 44 | 12 | 56 |
|   | Low | 372 | 79 | 451 |
| 25 | High | 110 | 64 | 174 |
|   | Low | 455 | 210 | 665 |
| 26 | High | 56 | 15 | 71 |
|   | Low | 559 | 132 | 691 |
| 28 | High | 44 | 7 | 51 |
|   | Low | 456 | 69 | 525 |
| 29 | High | 67 | 9 | 76 |
|   | Low | 553 | 62 | 615 |

Table 12 demonstrates the positive control group of gerbils' locomotor activity.

TABLE 12

| Animal Number | Beam Level (15 min) | Time (30 min.) | Time Total |
|---|---|---|---|
| 6 | High | 56 | 8  64 |
|   | Low | 290 | 68 358 |
| 75 | High | 43 | 19  62 |
|   | Low | 479 | 142 621 |
| 76 | High | 94 | 58 152 |
|   | Low | 1050 | 6831733 |

EXAMPLE 7

An extract of *Alaria esculenta* was prepared by boiling copped air dried leaves *Alaria esculenta* (50 g) in distilled water (1 Liter) for 6 hours hen allowed to cool to room temperature overnight. The swollen suspended Alaria leaves were press filtered and the filtrate concentrated by heating and evaporation to 350 mL. The concentrate was filtered through filter paper and measured at 370 nm for standardization.

200 μL of a 50% solution of the Alaria concentrate was measured on a microtitre plate reader and had an optical density of 2.06 at 370 nm.

This concentrate was used directly in measurements of LDL oxidation inhibition. The data from this synthesis is shown above in Example 4, Table 4.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. An amino acid-based compound of a general formula (I):

A—N(Z)—CH(R¹)C(O)—Q    (I)

wherein A is —C(CH₂OH)₃; Z is a hydrogen atom; R¹ is selected from the group consisting of a hydrogen atom and a methyl; and wherein Q is a substituent selected from the group consisting of —OCH₂CH₃, —SCH₂CH₃, —OCH₂CH₂Cl, —OCH₂CCl₃, —N(R²)₂, and —NR²N(R²)₂, wherein each R² is independently selected from the group consisting of a hydrogen atom, an alkyl group having from 1 to 3 carbon atoms, and a hydroxyalkl group having from 1 to about 3 carbon atoms.

2. A pharmaceutical antioxidant composition for administration to mammals, the pharmaceutical antioxidant composition comprising an amino acid-based compound of claim 1.

3. The pharmaceutical antioxidant composition according to claim 2, wherein Z is a hydrogen atom and R¹ is a hydrogen atom.

4. The pharmaceutical antioxidant composition according to claim 2, wherein Z is a hydrogen atom and R¹ is a methyl.

5. The pharmaceutical antioxidant composition according to claim 2, wherein the composition has no acute toxic effects at an oral dose of 1000 mg/Kg in rats after two weeks following oral administration.

6. The pharmaceutical antioxidant composition according to claim 2, wherein the composition has no acute toxic effects at an oral dose of 2000 mg/Kg in rats after two weeks following oral administration.

7. The pharmaceutical antioxidant composition according to claim 2, wherein the compound of the general formula (I) is capable of forming a stable nitroxide or nitroxyl radical at the N atom in formula (I).

8. The pharmaceutical antioxidant composition according to claim 2, wherein the composition is not toxic in mammals when administered in a therapeutically effective dose.

9. The pharmaceutical antioxidant composition according to claim 2, further comprising one or more additional antioxidants selected from the group consisting of ω-3-unsaturated fatty acids, polyphenols, vitamin E, bioflavinoids and proanthocyanidins.

10. The pharmaceutical antioxidant composition according to claim 2, wherein the pharmaceutical antioxidant composition is prepared for oral administration.

11. The pharmaceutical antioxidant composition according to claim 2, wherein the amino acid-based compound is derived from a natural source.

12. The pharmaceutical antioxidant composition according to claim 11, wherein the natural source is an extract of brown seaweed.

13. The pharmaceutical antioxidant composition according to claim 12, wherein the brown seaweed is selected from the group consisting of *Petalonia fascia, Alaria esceulenta* and *Scytosiphon dotyi*.

14. A method of treating antioxidant-responsive diseases in mammals, the method comprising administering a pharmaceutical antioxidant composition comprising a therapeutically effective amount of an amino acid-based compound of a general formula (I):

A—N(Z)—CH(R¹)C(O)—Q    (I)

wherein A is selected from the group consisting of

XO—[C(R²)₂]ₙ—    (1)

wherein n is an integer of from 1 to about 3,

X is selected from the group consisting of a hydrogen atom, an acyl group and a halogenated acyl group, and each R² is independently selected from the group consisting of a hydrogen atom, an alkyl group having from 1to about 3 carbon atoms, a hydroxyalkyl group having from 1 to about 3 carbon atoms, and CH₂OX; and

—C(CH₂OH)₃;    (2)

and wherein Z is selected from the group consisting of a hydrogen atom, an alkyl group of from 1 to about 3 carbon atoms, and A; R¹ is an amino acid side chain group; and wherein Q is a substituent selected from the group consisting of a hydroxyl, —N(R²)₂, —NR²N(R²)₂, —SR², an alkoxy, a halogenated alkoxy, an O-acyl, and an O-halogenated acyl.

15. The method according to claim 14, wherein the pharmaceutical antioxidant composition is administered orally.

16. The method according to claim 14, wherein the amino acid-based compound is selected from the group consisting of monocine, bicine, dicine, tricine, tricine thioethyl ester, tricine ethyl ester, tricine chloroethyl ester, tricine trichloroethyl ester, tricine amide, tricine hydrazide, N-hydroxypropyl glycine, 2-carboxy-5-hydroxymethyl-pyrrolidine and 2-carboxy-6-hydroxymethyl-piperidine.

17. The method according to claim 14, wherein Q is selected from the group consisting of —OH, —OCH₂CH₃, —SCH₂CH₃, —OCH₂CH₂Cl, —OCH₂CCl₃, —NH₂ and NHNH₂.

18. The method according to claim 14, wherein the amino acid-based compound is selected from the group consisting of monocine, bicine and tricine.

19. The composition of claim 2, further comprising a pharmaceutically acceptable carrier.

20. The method of claim 14, wherein the disease is selected from atherosclerosis, restenosis and stroke.

21. A method of treating diseases induced by the proliferation of vascular smooth muscle cells, comprising administering a pharmaceutical antioxidant composition comprising a therapeutically effective amount of an amino acid-based compound as an active ingredient having a general formula (1):

A—N(Z)—CH(R')C(O)—Q    (I)

wherein A is selected from the group consisting of

XO—[C(R²)₂]ₙ—    (1)

wherein n is an integer of from 1 to about 3,

X is selected from the group consisting of a hydrogen atom, an acyl group and a halogenated acyl group, and each R² is independently selected from the group consisting of a hydrogen atom, an alkyl group having from 1 to 3 carbon atoms, a hydroxyalkyl group having from 1 to about 3 carbon atoms, and $CH_2OX$; and $$—C(CH_2OH)_3 \qquad (2)$$

and wherein Z is selected from the group consisting of a hydrogen atom, an alkyl group of from 1 to about 3 carbon atoms, and A;

$R^1$ is an amino acid side chain group and

Q is selected from the group consisting of a hydroxyl, $—N(R^2)_2$, $—NR^2N(R^2)_2$, $—SR^2$, an alkoxy, a halogenated alkoxy, an O-acyl and an O-halogenated acyl.

22. The method of claim 21, wherein the proliferation of vascular smooth muscle cells is a result of coronary angioplasty.

23. The method of claim 21, wherein the administration is per-oral.

24. The method of claim 23, wherein said active ingredient is selected from the group consisting of monocine, bicine and tricine.

25. The method according to claim 14, wherein the active ingredient is derived from brown seaweed.

26. The method according to claim 22, wherein the active ingredient is derived from brown seaweed.

27. The method according to claim 25, wherein the brown seaweed is selected from the group consisting of *Alaria esculenta, Petalonia fascia* and *Scytosiphon dotyi*.

28. The method according to claim 26, wherein the brown seaweed is selected from the group consisting of *Alaria esculenta, Petalonia fascia* and *Scytosiphon dotyi*.

29. The method claim 19, wherein the antioxidant-responsive disease is selected from the group consisting of atherosclerosis, coronary artery disease, restenosis, osteoarthritis, reperfusion injury from blood clots, organic repair or organ transplants, neurodegenerative disease and stroke.

30. A method for treating, delaying the onset of, and/or preventing proliferation of vascular smooth muscle cells, comprising administering a composition according to claim 2.

31. The method of claim 30, wherein the proliferation of vascular smooth muscle cells is a result of coronary angioplasty.

32. A method of treating, delaying the onset of and/or preventing antioxidant responsive diseases in mammals, the method comprising administering the composition of claim 2.

33. The method of claim 32, wherein the administration is per-oral.

34. The method of claim 22, wherein the antioxidant-responsive disease is selected from atherosclerosis, coronary artery disease, restenosis, osteoarthritis, reperfusion injury from blood clots, organic repair or organ transplants, neurodegenerative disease and stroke.

* * * * *